US012569621B2

(12) United States Patent
Joseph

(10) Patent No.: US 12,569,621 B2
(45) Date of Patent: Mar. 10, 2026

(54) SUB-ASSEMBLY FOR MEDICAMENT DELIVERY DEVICE, AND MEDICAMENT DELIVERY DEVICE COMPRISING THE SUB-ASSEMBLY

(71) Applicant: SHL MEDICAL AG, Zug (CH)

(72) Inventor: Abhilash Joseph, Gustavsberg (SE)

(73) Assignee: SHL Medical AG, Zug (CH)

( * ) Notice: Subject to any disclaimer, the term of this patent is extended or adjusted under 35 U.S.C. 154(b) by 790 days.

(21) Appl. No.: 17/911,015

(22) PCT Filed: Mar. 16, 2021

(86) PCT No.: PCT/EP2021/056642
§ 371 (c)(1),
(2) Date: Sep. 12, 2022

(87) PCT Pub. No.: WO2021/204499
PCT Pub. Date: Oct. 14, 2021

(65) Prior Publication Data
US 2023/0098277 A1      Mar. 30, 2023

(30) Foreign Application Priority Data

Apr. 7, 2020    (EP) ..................................... 20168418

(51) Int. Cl.
*A61M 5/20*          (2006.01)
*A61M 5/32*          (2006.01)
(52) U.S. Cl.
CPC ............ *A61M 5/20* (2013.01); *A61M 5/3271* (2013.01)
(58) Field of Classification Search
CPC ........ A61M 5/2033; A61M 2005/2013; A61M 5/3271; A61M 5/20
See application file for complete search history.

(56) References Cited

U.S. PATENT DOCUMENTS 11,623,045 B2 *   4/2023   Chu ..................... A61M 5/3155
                                                    604/136
11,707,574 B2 *   7/2023   Holmqvist ......... A61M 5/31511
                                                    604/208
(Continued)

FOREIGN PATENT DOCUMENTS

WO        2011/123024 A1    10/2011
WO        2016/169748 A1    10/2016
(Continued)

OTHER PUBLICATIONS

International Search Report and Written Opinion for Int. App. No. PCT/EP2021/056642, mailed May 19, 2021.

*Primary Examiner* — Cris L. Rodriguez
(74) *Attorney, Agent, or Firm* — McDonnell Boehnen Hulbert & Berghoff LLP

(57)          ABSTRACT
A sub-assembly for medicament delivery device is presented having a plunger rod, a biasing member, a main body arranged to receive the plunger rod and the biasing member and comprising a holding member and a coupling member arranged to be rotatable relative to the main body. One of the main body and the coupling member includes a first engagement element having a protrusion extending substantially radially and the other one of the main body and the coupling member has a second engagement element which can be engaged with the protrusion such that the protrusion of the first engagement element is engaged with the second engagement element to form a snap-fit coupling to restrict the movement of the coupling member relative to the main body in a proximal direction when the holding member is in the holding position.

20 Claims, 9 Drawing Sheets

(56)                        References Cited

U.S. PATENT DOCUMENTS

|  |  |  |  |
|---|---|---|---|
| 12,115,361 B2 * | 10/2024 | Boström | ............. A61M 5/3213 |
| 2007/0135767 A1 | 6/2007 | Gillespie et al. | |
| 2015/0367072 A1 | 12/2015 | Constantineau et al. | |
| 2016/0303327 A1 | 10/2016 | Moren | |
| 2018/0104414 A1 | 4/2018 | Karlsson et al. | |
| 2018/0104415 A1 * | 4/2018 | Boström | ............. A61M 5/31511 |
| 2019/0201612 A1 * | 7/2019 | Klintenstedt | ........... A61M 5/24 |

FOREIGN PATENT DOCUMENTS

|  |  |  |  |  |
|---|---|---|---|---|
| WO | 2018/206583 A1 | 11/2018 | | |
| WO | WO-2020015984 A2 * | 1/2020 | .............. A61M 5/20 |
| WO | WO-2020015985 A1 * | 1/2020 | .......... A61M 5/3213 |
| WO | WO-2020015986 A1 * | 1/2020 | .......... A61M 5/3213 |

* cited by examiner

Fig. 2A
-- Prior Art --
Fig. 3A
-- Prior Art --
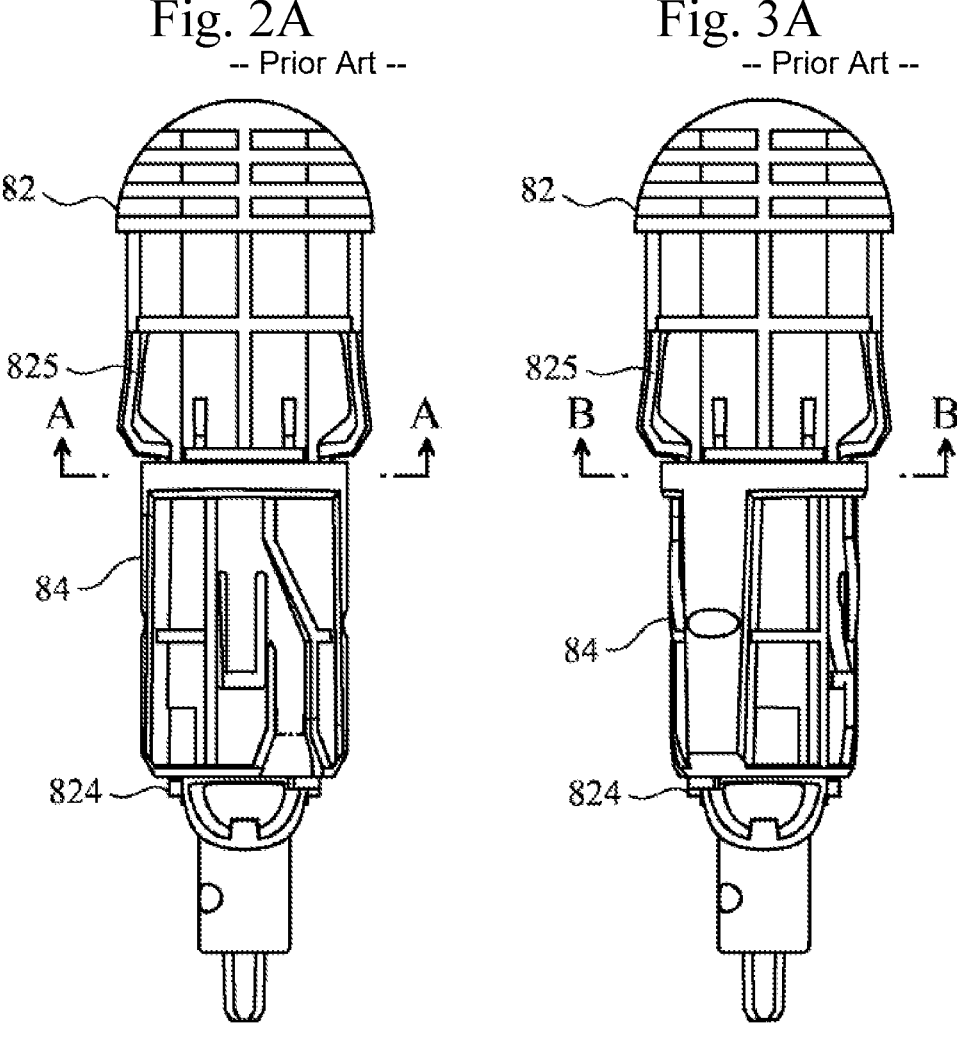
Fig. 2B
-- Prior Art --
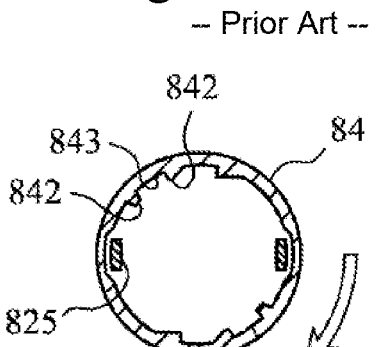
Fig. 3B
-- Prior Art --
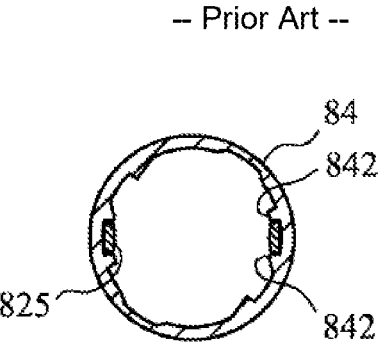

82

825

828

84

61

Fig. 11A
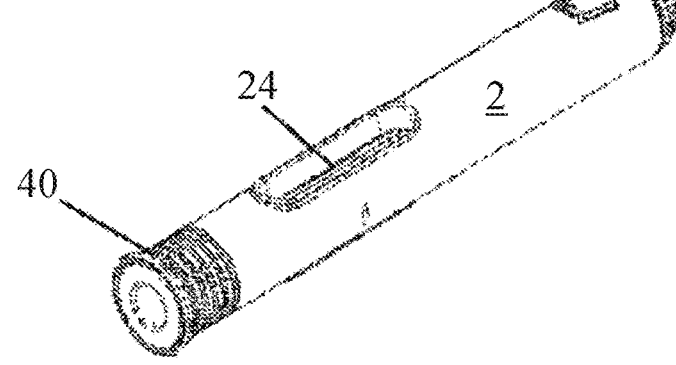
Fig. 11B
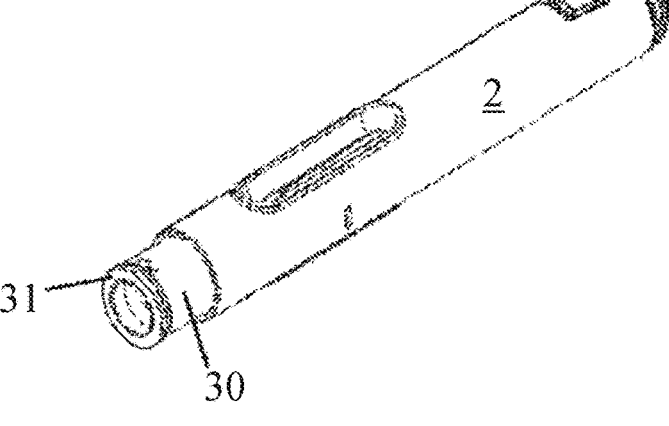
Fig. 11C
Fig. 11D
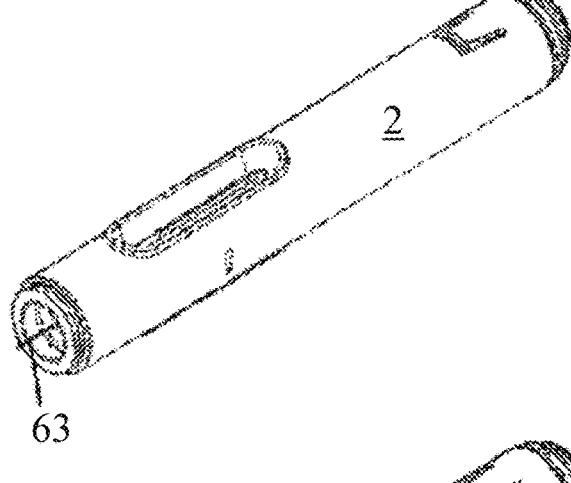

SUB-ASSEMBLY FOR MEDICAMENT DELIVERY DEVICE, AND MEDICAMENT DELIVERY DEVICE COMPRISING THE SUB-ASSEMBLY

CROSS REFERENCE TO RELATED APPLICATIONS

The present application is a U.S. National Phase Application pursuant to 35 U.S.C. § 371 of International Application No. PCT/EP2021/056642 filed Mar. 16, 2021, which claims priority to European Patent Application No. 20168418.0 filed Apr. 7, 2020. The entire disclosure contents of these applications are herewith incorporated by reference into the present application.

TECHNICAL FIELD

The present disclosure generally relates to a sub-assembly of medicament delivery device comprising a transportation locking mechanism, and a medicament delivery device comprising the sub-assembly.

BACKGROUND

Many medicament delivery devices have been developed for users to perform the medicament delivery on their own. Document WO 2011/123024 (referred as "WO '024" in the following) and WO 2016/169748 (referred as "WO '748" in the following) disclose such medicament delivery devices.

A medicament delivery device and a sub-assembly for the device according to WO '748 was proposed to resolve the problem that a delivery actuation means included in the sub-assembly of medicament delivery device according to WO '024 is actuated while the sub-assembly is being transported for the final assembly. Specifically, a plunger rod in WO '024 may be catapulted by disengagement between a recess on the plunger rod and a protrusion engaged with the recess during transportation (see FIGS. 4C and 5 of WO '024). This disengagement may be caused by force unintentionally applied to the sub-assembly during transportation.

FIGS. 1 to 4 show a sub-assembly 8 including a delivery actuation means according to WO '748. Key structural elements in WO '748 for resolving the problem are flexible tabs 825 oppositely arranged in a main body 82, and recesses 843 and protrusions 842 formed on an inner surface of a coupling member 84.

Each flexible tab 825 has a cantilever structure. One end of the flexible tab 825 is fixed to the main body 82, and the other end is a free end. A proximal half of the tab 825 extends radially outwards from the longitudinal axis of the main body 82, and then extends radially inwards to form an arch 828. A distance between the arch 828 and the central axis of the main body 82 is larger than a distance between other portions of the tab 825 and the central axis, than an outer radius of the coupling member 84, and also than an inner radius of a housing 61 into which the sub-assembly is inserted for the final assembly of the medicament delivery device.

When the coupling member 84 is mounted on and then rotated relative to the main body 82, the free end of the tab 825 snaps into the recess 843 along with being bent radially inwards. In this coupling state, due to the engagement between the free end of the flexible tab 825 and the recess 843, the coupling member 84 is prevented from rotating relative to the main body 82. Since the coupling member 84 is rotationally locked to the main body 82, a holding member (flexible arm) 823 can be confined by the coupling member 84, and a free end of the flexible arm 823 can maintain the state of locking a plunger rod 81 by being engaged with an engagement hole 86 on the plunger rod 81.

After transportation, the sub-assembly 8 is assembled with other sub-assemblies to form the final assembly of the medicament delivery device. In the final assembly, most parts of the sub-assembly 8 are inserted into a housing 61. As shown in FIG. 4, an inner surface of the housing 61 bends the flexible tab 825 radially inwards to the extent that the free end of the flexible tab 825 is totally released from the recess 843. Therefore, the coupling member 84 becomes ready to be rotated by interactions between rotation guides 846, 847 formed on an outer surface of the coupling member 84, and protrusions (not shown) formed on an element moving linearly along the housing 61 when the medicament delivery device is in the injection state.

However, the sub-assembly and the medicament delivery device proposed by WO '748 have some problems.

In the structure of the sub-assembly in WO '748, an axial location of the coupling member 84 relative to the main body is important to ensure the engagement between the free end of the flexible tab 825 and the recess 843 in the distal end portion of the coupling member 84. This relative axial position of the coupling member 84 is maintained by protrusions 824 located at a proximal end portion of the main body 82. The protrusions 824 are located remote from the location at which the coupling member 84 and the free end of the flexible tab 825 are engaged. Thus, the relative axial position between the coupling member 84 and the free end of the flexible tab 825 may be out of the pre-set range, such that the free end of the flexible tab 825 and the coupling member 84 may not be engaged securely.

Further, the inventor of the present disclosure found that the protrusions 824 are under the risk of breakage or wear by interference with the coupling member 84 since the protrusions 824 continuously exert forces on the coupling member 84 to restrict the axial movement of the coupling member 84. In some situations, broken plastic parts originating from the protrusions 824 may be stuck between the plunger 81 and a syringe (not shown), and cause failure on the delivery of medicament. Such risk of breakage or wear of the protrusions 824 may also exist due to interference of the protrusions 824 with a U-bracket (not shown). The U-bracket supports an end of a resilient member 83 and is inserted into the main body 82 together with the resilient member 83 and the plunger rod 81. End tips of the U-bracket are seated adjacent to or on the protrusions 824. Since the U-bracket is made of steel material and the main body 82 is made of plastic material, movement of the end tips of the U-bracket in relation to the protrusions 824 may damage the protrusions 824, generating plastic particles.

SUMMARY

The following description and drawings disclose embodiments of the present disclosure and their implementation variations. The scope of protection is defined by the claims, to which reference should now be made.

In the present disclosure, when the term "distal" is used, this refers to the direction pointing away from a dose delivery site where a dose of medicament is delivered. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component. In a similar manner, the terms "radial" or "transversal", with or without "axis", refers to a direction or an axis through the device or components thereof in a direction generally perpendicular to the longitudinal direction. For instance, the term "radially outward" would refer to a direction pointing away from the longitudinal axis.

According to the disclosure in the following description and drawings, there is provided a sub-assembly for a medicament delivery device, comprising a plunger rod; a biasing member, at least a portion of which is accommodated in the plunger rod and which applies force biasing the plunger; a main body arranged to receive the plunger rod and the biasing member and comprising a holding member; a coupling member arranged to be rotatable relative to the main body. The holding member is configured to have, at least, a holding position in which the holding member is engaged with the plunger rod, and a releasing position in which the holding member is not engaged with plunger, the holding member being switchable from the holding position to the releasing position depending on rotational positions of the coupling member relative to the main body. One of the main body and the coupling member comprises a first engagement element having a protrusion extending substantially radially, and the other one of the main body and the coupling member has a second engagement element which can be engaged with the protrusion. The main body and the coupling member are configured such that the protrusion of the first engagement element are engaged with the second engagement element to form a snap-fit coupling, at least when the holding member is in the holding position, the snap-fit coupling restricting the movement of the coupling member relative to the main body in a proximal direction. This can enable a pre-determined relative axial position between the coupling member 84 and the main body 82 to be maintained reliably even in cases when significant external forces are applied to the sub-assembly during transportation. Further, this can prevent generation of plastic particles from the protrusions 824 on the main body, such that the possibility of operation failure of the medicament delivery device due to the plastic particles can be reduced.

Preferably, one end of the first engagement element may be fixed to the main body and the other end of the first engagement element may be a free end.

Preferably, the first engagement element may comprise, at least, a third part connected to the main body and extending in the proximal direction, and a fourth part extending radially from an end of the third part and forming the free end, the fourth part being said protrusion.

Preferably, the first engagement element may further comprise a first part fixed to the main body and extending longitudinally in the proximal direction as well as radially outwards, and the second part extending radially inwards from an end of the first part and connected to the third part.

Preferably, the coupling member may include a rim surrounding a bore at a distal end portion thereof, the rim comprising a recess or hole formed along a circumferential direction of the rim, and the second engagement element may comprise a portion of the rim adjacent to the recess or hole.

Preferably, the coupling member may have two rotational positions, releasing rotational position and holding rotational position, relative to the main body, which respectively correspond to the releasing position and the holding position of the holding member. When the coupling member is in the releasing rotational position, the protrusion of the first engagement element may be engaged with the portion of the rim adjacent to the recess or hole.

Preferably, the coupling member may further include at least one protrusion which is formed on an inner surface of the rim and disposed between the distal end of the coupling member and the recess or hole. In this case, the second engagement element may comprise the protrusion. The protrusion of the first engagement element may be engaged with the protrusion of the coupling member, or with the protrusion and the rim of the coupling member together, adjacent to the recess or hole.

Preferably, when the coupling member is in the holding rotational position, the protrusion of the first engagement element is engaged with the protrusion of the coupling member, or with the protrusion and the rim of the coupling member together, adjacent to the recess or hole.

Preferably, when the coupling member is in the releasing rotation position, the protrusion of the first engagement element may not be engaged with the rim, or engaged with the rim only; and when the coupling member is in the holding rotation position, the protrusion of the first engagement element may be engaged at least with the protrusion of the coupling member.

Preferably, the coupling member may comprise a central through-hole into which the main body can be inserted, and a longitudinal groove which can guide the insertion of the main body into the coupling member. Further, the coupling member may be rotatable relative to the main body when the main body is inserted into the coupling member along the longitudinal groove up to a pre-determined fully-inserted position.

Preferably, the coupling member may be in the releasing rotational position when the main body is inserted into the coupling member up to the pre-determined fully-inserted position. Further, the coupling member may be in the holding rotational position when the coupling member is rotated in a first rotational direction by a pre-set angle from the pre-determined fully-inserted position.

Preferably, the at least one protrusion of the coupling member may include two protrusions which form a recess between the two protrusions. Further, the first engagement element may be disposed to be in or face the recess when the main body is inserted into the coupling member up to a pre-determined fully-inserted position.

Preferably, one of the two protrusions not engaged with the protrusion of the first engagement element may have a wall-shaped surface which is configured to restrict a movement of the first engagement element in a rotational direction of the coupling member.

Preferably, the protrusion of the coupling member arranged to be engaged with the protrusion of the first engagement element may have a ramp-shaped surface which interferes with the first engagement element and thereby guides the protrusion of the first engagement element to move radially inwards while the coupling member is rotated.

Preferably, the recess or hole may have a radial edge which restricts a movement of the protrusion of the first engagement element in a rotational direction of the coupling member.

According to the disclosure in the following description and drawings, there is also provided a medicament delivery device such as an autoinjector comprising a sub-assembly as described above. Preferably, the medicament delivery device comprises: a casing; an activation member disposed in the casing and linearly movable along the longitudinal direction of the casing; a medicament container disposed inside the activation member, containing medicament, and comprising a slidable stopper arranged to expel the medicament out of the medicament container, and a medicament delivery member such as a needle connected with a proximal end portion of the medicament container; a resilient member arranged to apply force to move the activation member in the proximal direction of the medicament delivery device; and the sub-assembly mentioned above. Further, the sub-assembly is coupled to the distal end of the casing, arranged to push the slidable stopper when the plunger rod is released, and comprises a means of restricting a second movement of the activation member in the distal direction of the medicament delivery device after the activation member has moved in the distal direction.

The medicament delivery device may be an injection device.

There is also provided a sub-assembly for a medicament delivery device comprising a plunger rod, a biasing member configured to bias the plunger rod, a main body arranged to receive the plunger rod and the biasing member and comprising a holding member and a coupling member (rotator) arranged to be rotatable relative to the main body. The sub-assembly comprises a lock, wherein the lock comprises a lock member arranged at the distal end of the coupling member and a second lock member on the main body. The lock restricts or stops movement of the coupling member in the axial direction. The lock also restricts or stops the coupling member from rotating when the sub-assembly is being transported prior to final assembly.

BRIEF DESCRIPTION OF THE DRAWINGS

The accompanying drawings, which are included to provide a further understanding of the present disclosure and constitute a portion of the specification, illustrate embodiments of the present disclosure, and together with the description serve to explain the principle of the present disclosure.

FIG. 2 is an assembled plain view of the sub-assembly of FIG. 1 illustrating a state that the coupling member 84 is not locked by the flexible tab 825;

FIG. 2B is a sectional view of FIG. 2 taken along a line A-A;

FIG. 3 is an assembled plain view of the sub-assembly of FIG. 1 illustrating a state that the coupling member 84 is locked by the flexible tab 825;

FIG. 3B is a sectional view of FIG. 3 taken along a line B-B;

FIGS. 11A to 11D are perspective views of different states of the medicament delivery device which includes the sub-assembly according to the present disclosure.

DETAILED DESCRIPTION

Figure 1:
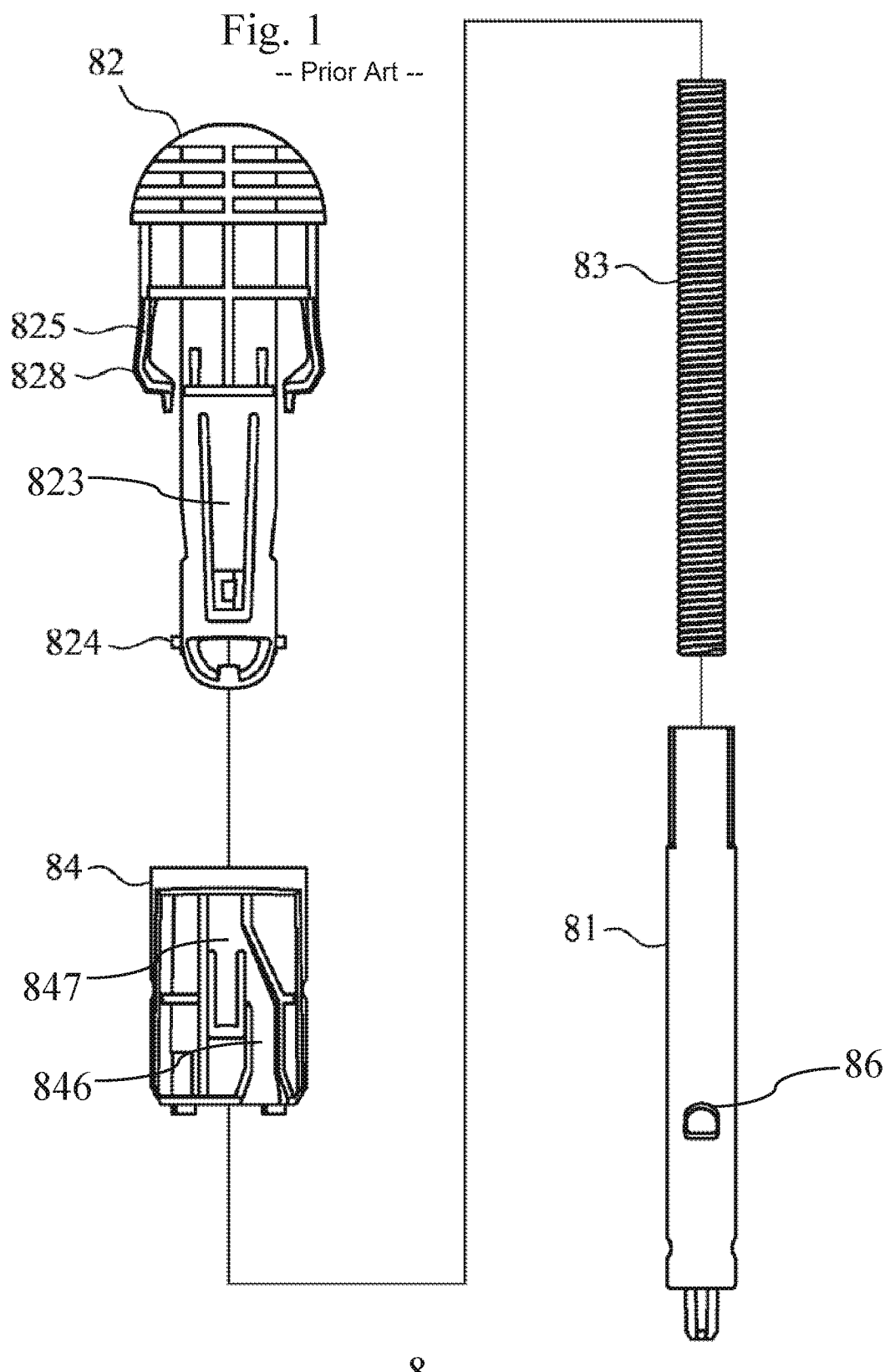
FIG. 1 is an exploded plain view of a sub-assembly disclosed in WO '748.
Figure 4:
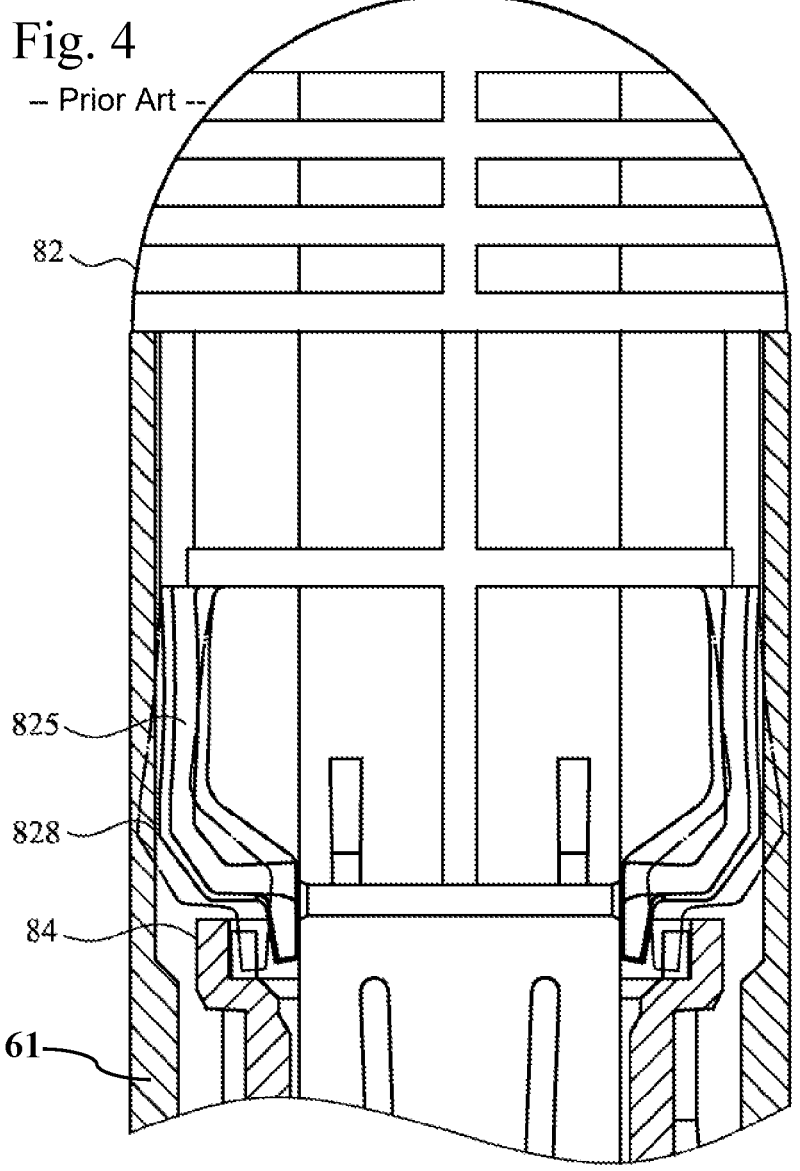
FIG. 4 is a partially enlarged sectional view illustrating different positions of the flexible tab 825 when the sub-assembly of FIG. 1 is inserted into the housing 61 for the final assembly of the medicament delivery device.
Figure 5:
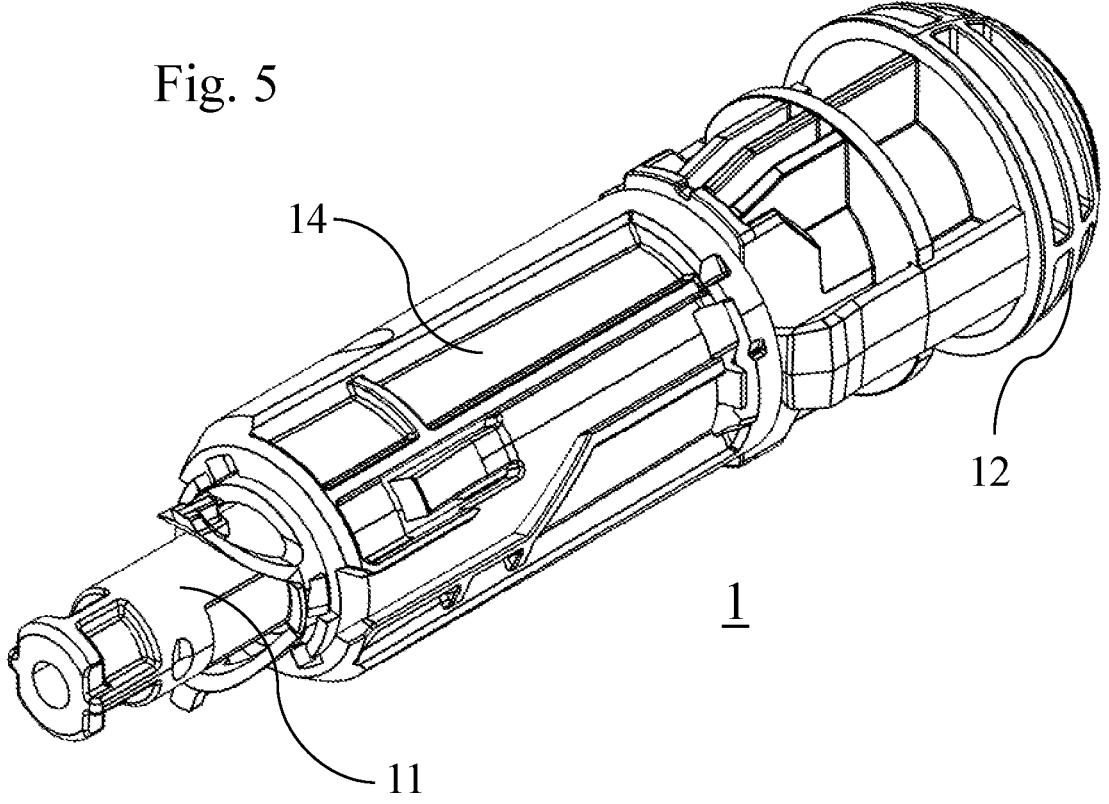
FIG. 5 is an assembled perspective view of a sub-assembly according to a first embodiment of the present disclosure.
Figure 6:
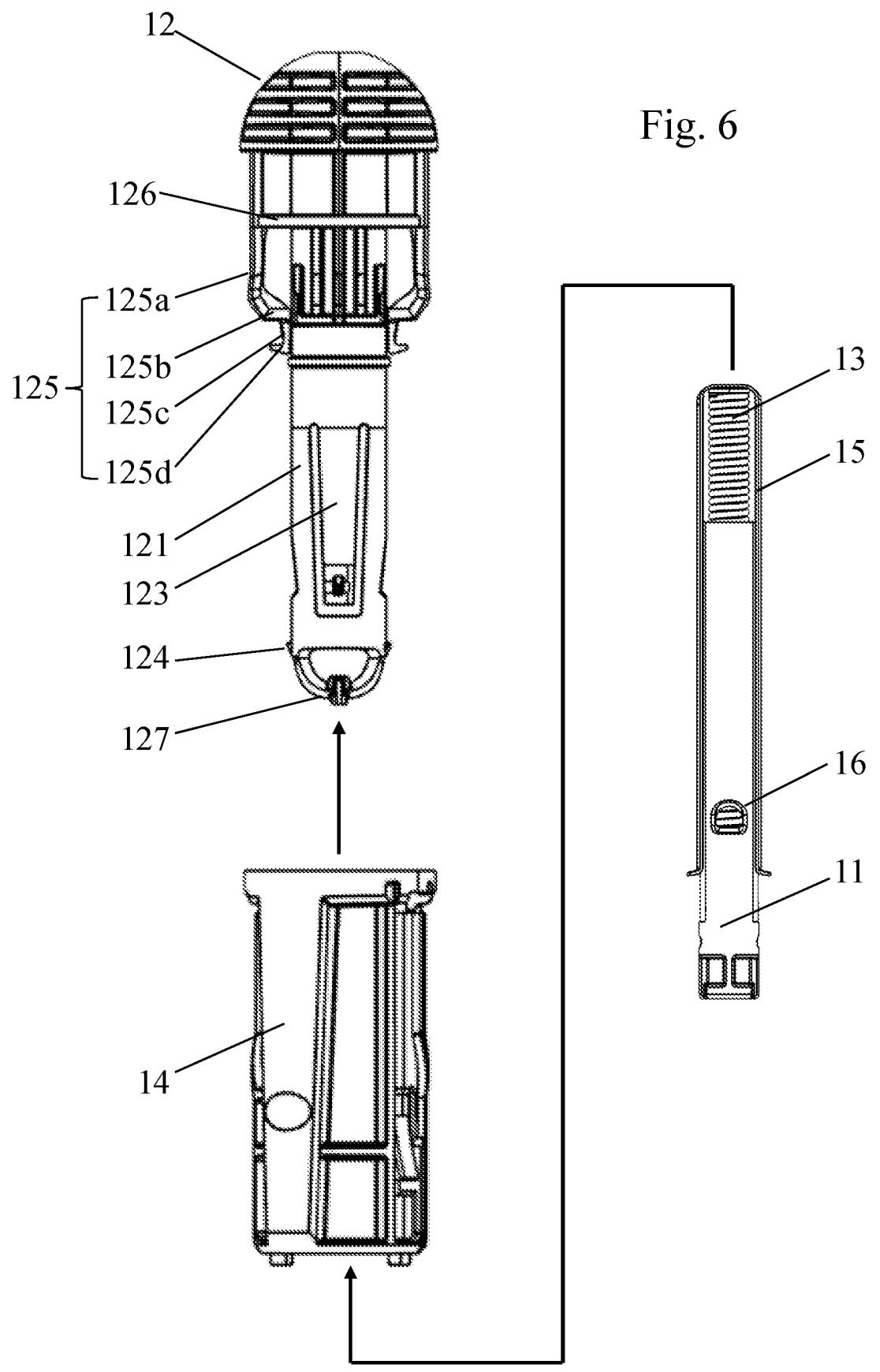
FIG. 6 is an exploded plain view of the sub-assembly according to the first embodiment of the present disclosure.
Figure 7:
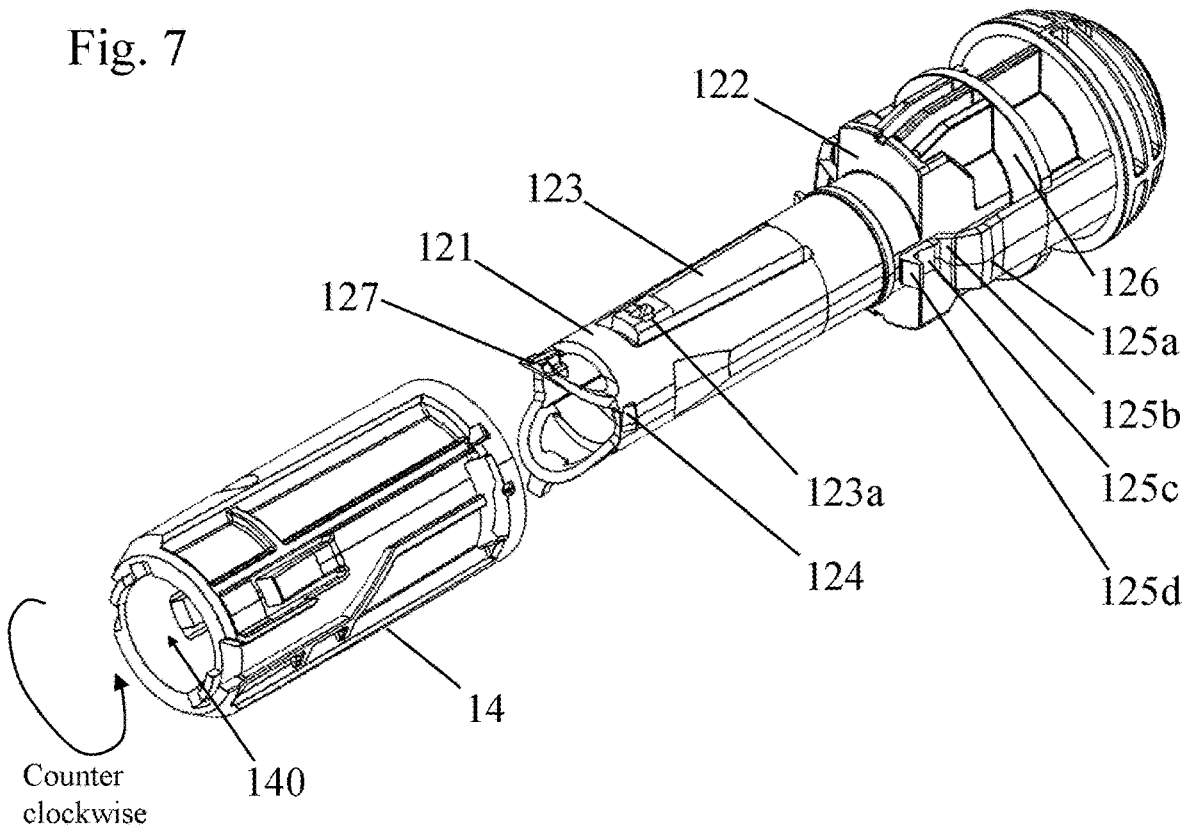
FIG. 7 is an exploded perspective view of a coupling member and a main body according to the first embodiment of the present disclosure.

FIGS. 5, 6, 7, 8, 9A and 9B show a sub-assembly 1 of medicament delivery device according to a first embodiment of the present disclosure.

The sub-assembly 1 comprises a plunger rod 11 having an engagement hole 16, a main body 12 which slidably receives the plunger rod 11, a biasing member 13 which is accommodated radially in the plunger rod 11 for biasing the plunger rod 11, and a coupling member 14 arranged to be radially moveable relative to the main body 12. The biasing member 13 may be a tension spring, but is not limited to this. A U-bracket 15 may be further installed to partially enclose the biasing member 13 and the plunger rod 11. The U-bracket 15 guides the releasing motion of the plunger rod 11 and the biasing member 13.

The main body 12 comprises a hollow cylinder 121. A rib 122 is arranged to radially extend from the cylinder 121 and divides the hollow cylinder 121 into a proximal section and a distal section. A holding member 123 is formed in the proximal section and constitutes a portion of the hollow cylinder 121. The figures show a flexible arm on the cylinder 121 as the holding member 123, but the present disclosure is not limited to this specific type. The holding member 123 is configured to be directly connected to the plunger rod 11 to hold the biased plunger rod 11 until the medicament delivery device is activated. A projection 124 may be arranged to extend radially from a proximal end of the proximal section of the hollow cylinder 121. However, according to the present disclosure, as explained below, the installation of the projection 124 is not necessarily required. At least one guide protrusion 127 is formed on the proximal end of the main body 12. The guide protrusion 127 works for determining an angular position of the main body 12 relative to the coupling member 14 when the main body 12 and the coupling member 14 are assembled together.

At least one first engagement element 125 longitudinally extends proximally from the distal section. The main body 12 has two first engagement elements 125 which are oppositely arranged relative to the longitudinal axis. A radial wall 126 extends radially outward from the cylinder 121 and abuts a distal portion of the first engagement element 125 to radially support the first engagement element 125.

One end of the first engagement element 125 is fixed to the distal section of the main body 12, and the other end is a free end. The first engagement element 125 comprises a first part 125a extending longitudinally in the proximal direction as well as extending radially outwards relative to the fixed end, a second part 125b extending radially inwards from an end of the first part 125a, a third part 125c extending longitudinally in the proximal direction from an end of the second part 125b, and a fourth part 125d extending radially outwards from an end of the third part 125c and constituting the free end of the first engagement element 125. Particularly, the fourth part 125d extends from the third part 125c with a sharp angle, such that the fourth part 125d and the third part 125c forms a hook shape. A curved transition part may be added between the first and second parts 125a and 125b, between the second and third parts 125b and 125c, and/or between the third and fourth parts 125c and 125d. The longitudinal thickness of the fourth part 125d gets smaller toward the free end, i.e., tapers radially outwards.

Figure 8:
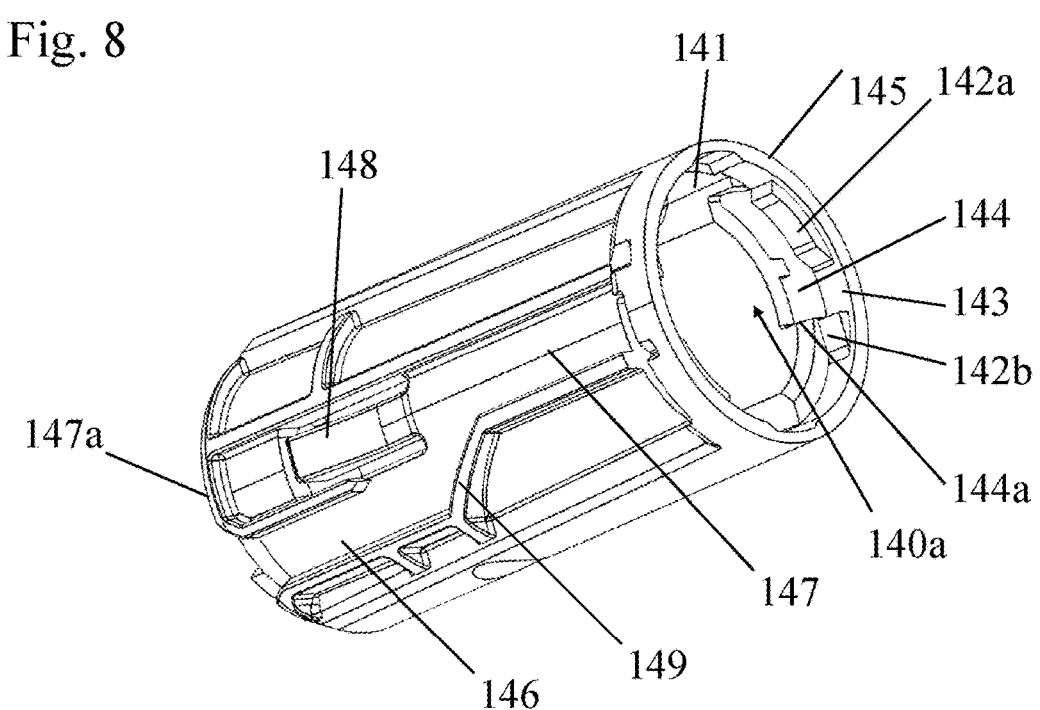
FIG. 8 is a perspective view of the coupling member according to the first embodiment of the present disclosure from a different perspective angle.

The coupling member 14 may include a central through-hole 140 into which the main body 12 can be inserted. The coupling member 14 may include a bore 140a at the distal end of the coupling member 14. Thus, the bore 140a forms a part of the central through-hole 140. The bore 140a is surrounded by a rim 145 having an inner diameter larger than diameters of the other parts of the central through-hole. A longitudinal groove 141 may be formed on an inner surface of the through-hole. At least two protrusions 142a, 142b extend radially inwards from an inner surface of the rim 145 at the distal end of the coupling member 14. A recess 143 may be formed between adjacent protrusions 142a, 142b. Each of the protrusions 142a, 142b may have a ramp-shaped first surface extending inwards from the inner surface of the rim 145 and a wall-shaped second surface extending substantially orthogonally from the inner surface of the rim 145. Alternatively, only one of the protrusions 142a may have such a first ramp-shaped surface and a second wall-shaped surface. The other protrusion 142b may have two wall-shaped surfaces. The longitudinal thickness of the protrusions 142a, 142b is smaller than the longitudinal length of the third part 125c of the first engagement element 125. In general in this application, the ramp-shaped and wall-shaped surfaces are defined relative to the circumferential direction, as can be seen in FIG. 8, for example. The ramp-shaped surface is therefore angled relative to both the circumferential direction and the radial direction, and the wall-shaped surface extends in (or substantially in) the radial direction.

A ramp-shaped surface of one of the protrusions 142a, 142b may guide the third part 125c of the first engagement elements 125 to move radially inwards while the coupling member 14 is being rotated relative to the main body. A wall-shaped surface of one of the protrusions 142a, 142b may restrict a rotational movement of the third part 125c while the coupling member 14 is rotated relative to the main body.

At least one hole 144 may be formed to extend circumferentially along the cylindrical body of the coupling member 14. The circumferentially-extended hole 144 allows the central through-hole to communicate with the outside of the coupling member 14 in a radial direction. The hole 144 is disposed adjacent to the protrusions 142a, 142b in the longitudinal direction of the coupling member 14. The hole 144 has, at least, two edges defining the circumferential boundary thereof. One edge 144a of the two edges may restrict a movement of the fourth part 125d of the first engagement element 125 in a rotational direction of the coupling member 14.

The coupling member 14 is mounted on the main body 12 by the main body 12 being inserted into the central through-hole of the coupling member 14. In order for the main body 12 to be inserted into the central through-hole of the coupling member 14, the longitudinal groove 141 of the coupling member 14 and the guide protrusion 127 of the main body 12 have to be angularly aligned first. After this alignment is made, the coupling member 14 can slide on the outer surface of the main body 12.

Figure 9A:
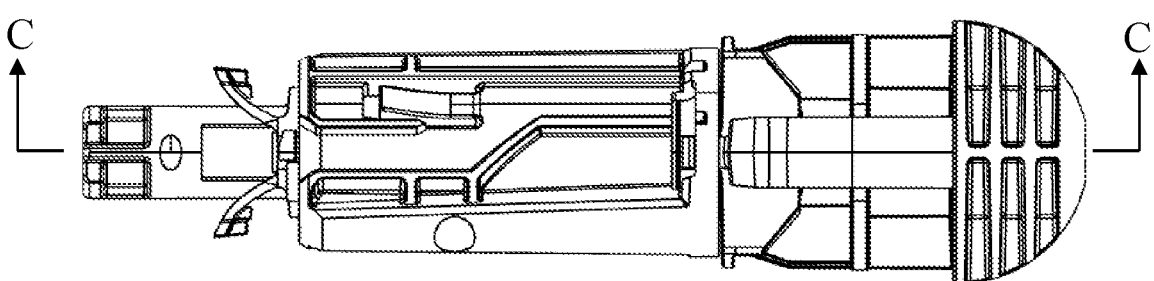
FIG. 9A is a plain side view of the sub-assembly according to the first embodiment of the present disclosure.
Figure 9B:
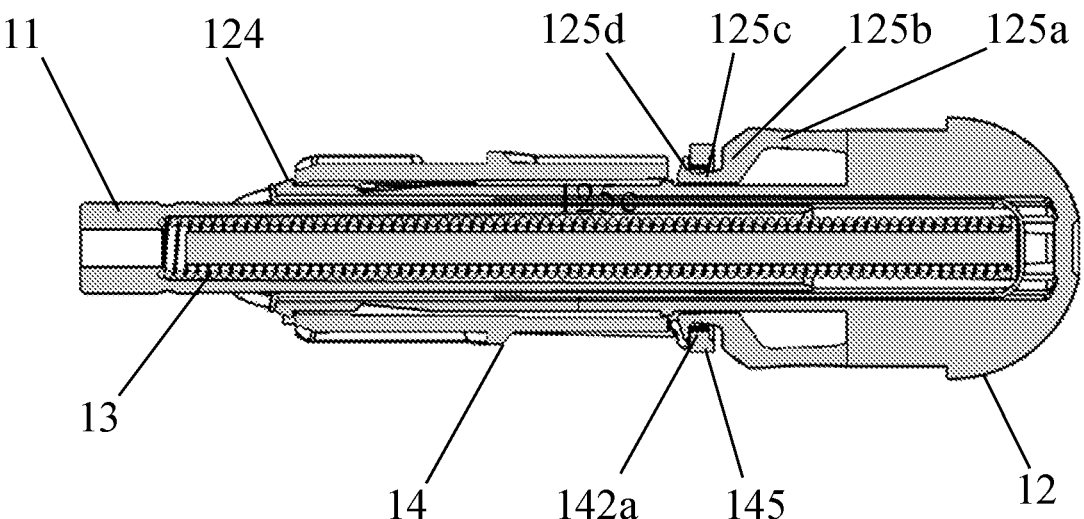
FIG. 9B is a sectional view of FIG. 9A taken along a line C-C.

When the main body 12 reaches a pre-determined fully-inserted position, a portion of the third part 125c of the first engagement element 125 is positioned in the recess 143, and the fourth part 125d faces or is inserted into the hole 144. Then, the coupling member 14 is rotated in the counter-clockwise direction (referred to in FIG. 7) at said pre-determined fully-inserted position of the main body 12. The portion of the third part 125c moves along the ramp-shaped first surface of the protrusion 142a and then is seated on an inner surface of the protrusion 142a. At the same time, the fourth part 125d of the first engagement element 125 also moves and is positioned to be engaged with the protrusion 142a. In this configuration, the radially outer surface of the third part 125c of the first engagement element 125 abuts the radially inner surface of the protrusion 142a, and the distal surface of the fourth part 125d abuts the proximal surface of the protrusion 142a. Hence, the fourth part 125d and protrusion 142a form a sort of snap-fit coupling as shown in FIG. 9B.

Due to this snap-fit coupling, the movement of the coupling member 14 in the proximal direction can be restricted. Thus, the axial position of the coupling member 14 relative to the main body 12 is reliably maintained, even in cases where unintentional axial forces are applied to the sub-assembly 1 during transportation. Further, since the third part 125c is elastically bent inwards by interference with the protrusion 142a, the third part 125c and the protrusion 142a are so tightly coupled by elastic force. In this state, the coupling member 14 is rotatable relative to the main body 12, but a relatively large force is required for initiating the relative rotation of the coupling member 14. Therefore, unintentional rotation of the coupling member 14 relative to the main body 12 during transportation can be prevented.

In the first embodiment, the projection 124 on the main body 12 may be removed, since the previous function of the projection 124, which restricts the movement of the coupling member 14 in the proximal direction, is performed by the snap-fit coupling. However, as a precautionary measure to restrict the movement of the coupling member 14 more reliably even in cases where the snap-fit coupling is broken, the projection 124 may be maintained.

Many different variations of this snap-fit coupling may be implemented.

Particularly, the length of the fourth part 125d of the first engagement element 125, an original molded shape of the first engagement element 125, and the radial thickness of the rim 145 may be designed in various ways.

In such a design variation, the fourth part 125d may become engaged with the rim 145 at the moment when the main body 12 is inserted into the coupling member 14 up to the pre-determined fully-inserted position. Then, the fourth part 125d becomes further strongly engaged with the protrusion 142a or with the protrusion 142a and the rim 145 together when the coupling member 14 is rotated in the counterclockwise direction from the pre-determined fully-inserted position.

In another design variation, the fourth part 125*d* may not be engaged with the rim 145 at the moment when the main body 12 is inserted into the coupling member 14 up to the pre-determined fully-inserted position. Then, after the relative clockwise rotation of the coupling member 14 to the main body 12, the fourth part 125*d* may be engaged with the protrusion 142*a* or with the protrusion 142*a* and the rim 145 together.

In another variation, the fourth part 125*d* as well as the third part 125*c* of the first engagement element 125 may not be engaged with the rim 145 at the moment when the main body 12 is inserted into the coupling member 14 up to the pre-determined fully-inserted position. Then, only when the coupling member 14 is rotated in the counterclockwise direction from the pre-determined fully-inserted position, the third part 125*c* may abut the protrusion 142*a*, and the fourth part 125*d* may be engaged at least with the protrusion 142*a*, resulting in the snap-fit coupling. In this variation, the elastic force radially applied on the protrusion 142*a* may be less than the above-mentioned variation. However, elastic force sufficient for preventing unintentional rotation of the coupling member 14 relative to the main body 12 can be obtained.

In the above-mentioned variations, the rim 145 and/or the protrusion 142*a* may be engaged with the fourth part 125*d* of the first engagement element 125. The rim 145, the protrusion 142*a*, and a combination of the rim 145 and the protrusion 142*a* are collectively referred to as a second engagement element.

In another variation, the circumferentially-extended hole 144 may be replaced with a recess or a groove as far as this recess or groove provides a sufficient space for at least a portion of the fourth part 125*d* of the first engagement element 125 to be accommodated.

In another variation, the snap-fit coupling may be made by the fourth part 125*d* and the rim 145, instead of the protrusion 142*a*. For this variation, the radial width of the rim 145 as well as the radial length of the fourth part 125*d* may be adjusted accordingly. In this variation, the protrusion 142 may be removed, or re-arranged only for the function of guiding the axial movement of the fourth part 125*d* when the main body 12 reaches close to the pre-determined fully-inserted position.

In another variation, the structure of the first engagement element 125 may be made simpler to the extent that the first engagement element 125 provides a protrusion applicable for the snap-fit coupling. For instance, the first engagement element 125 may have only two parts, a first part extending proximally and a second part extending radially outwards. This second part may be such a protrusion applicable for the snap-fit coupling. To be further simpler, the first engagement element 125 may have only one part extending radially outwards. Even in this case, the snap-fit coupling can be made by extending a part of the distal end of the coupling member 14. Therefore, in the first embodiment, the first, second and third parts 125*a*, 125*b* and 125*c* of the first engagement element 125 in the present disclosure are not essential for achieving the results of the present disclosure. However, the existence of the first, second and third parts 125*a*, 125*b* and 125*c* contributes to increasing the degree to which the fourth part 125*d* can be bent or move radially inwards.

In another variation, a protrusion of the first engagement element 125 applicable for the snap-fit coupling may extend radially inwards, not outwards. A recess or hole having a boundary surface capable of being engaged with the protrusion may be arranged such that the protrusion faces a radially outer surface of the recess in case of the recess, or an inner space of the coupling member 14 in case of the hole.

In a second embodiment (not illustrated) of the present disclosure, the snap-fit coupling is made in the other way around. Namely, a first engagement element having at least parts corresponding to the third and fourth parts 125*c*, 125*d* is formed on the coupling member 14, and a coupling hole or protrusion corresponding the hole 144 or the protrusion 142*a* is formed in the main body 12. Preferably, in this embodiment, the first engagement element may have an end fixed to a distal section of the coupling member 14, and another end, which is a free end extending distally. The coupling hole or protrusion corresponding the hole 144 or the protrusion 142*a* may be installed at the distal section of the main body 12.

By the way, when the coupling member 14 starts to be rotated in the counterclockwise direction (referred to in FIG. 7) after the main body 12 is inserted into the coupling member 14 up to the pre-determined axial position, an inner edge of the longitudinal groove 141 interferes with an edge 123*a* of the flexible arm 123. By further rotation of the coupling member 14, an inner surface of the central through-hole of the coupling member 14 rides upon the flexible arm 123 and moves an end of the flexible arm 123 radially inwards into the engagement hole 16 of the plunger rod 11. After that, when a sub-assembly consisting of the biasing member 13, the plunger 11 and the U-bracket 15 is inserted into the cylinder 121 of the main body 12, the inward-moved end of the flexible arm 123 can hold the plunger rod 11 until being released for injection of medicament.

Thus, the flexible arm 123 has two positions. The first one is a holding position, in which the flexible arm 123 is engaged with the plunger rod 11, and which is provided when the coupling member 14 is at a first rotational position (referred to as "a holding rotational position") relative to the main body 12. The second one is a releasing position, in which the flexible arm 123 is not engaged with the plunger rod 11, and which is provided when the coupling member 14 is at a second rotational position (referred to as "a releasing rotational position") relative to the main body 12. The first and second rotational positions are different from each other.

At the moment when the main body 12 is inserted into the coupling member 14 straight along the longitudinal groove 141 up to the pre-determined fully-inserted position, the flexible arm 123 may be in the releasing position. At the moment when the inner surface of the coupling member 14 rides on the flexible arm 123 after the relative counterclockwise rotation of the coupling member 14, the flexible arm 123 may be in the holding position.

Figure 10A:
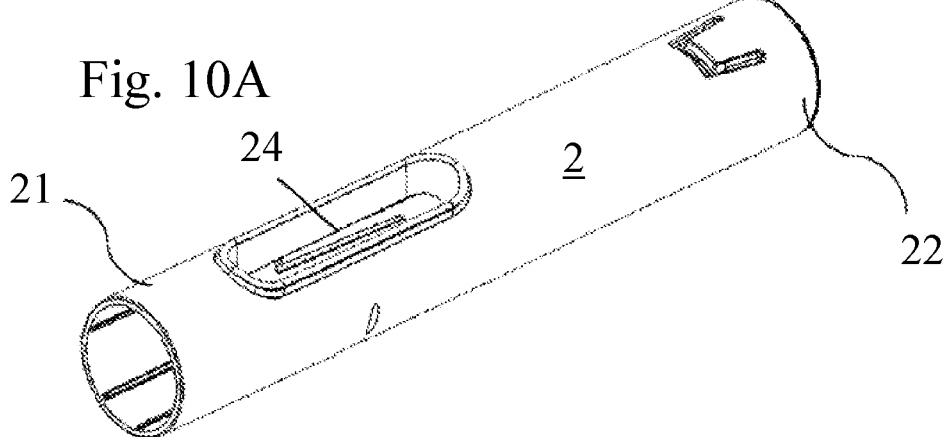
FIGS. 10A to 10C are perspective views of different components of a medicament delivery device which includes the sub-assembly according to the present disclosure.
Figure 10B:
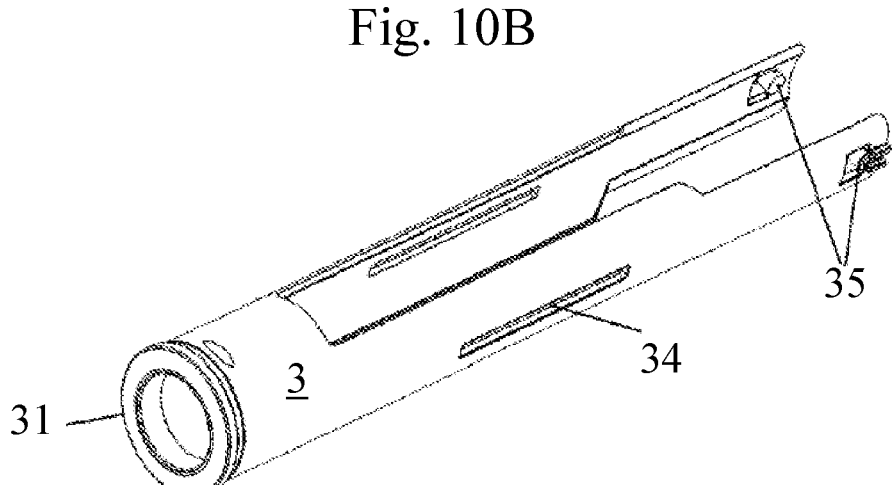
Figure 10C:
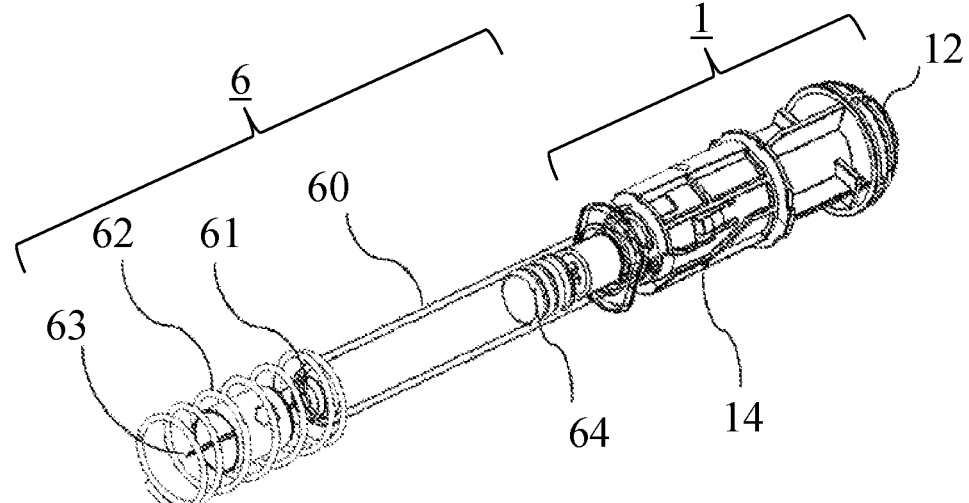

FIGS. 10A to 10C show different components assembled for the final assembly of a medicament delivery device, which includes the sub-assembly according to the present disclosure.

Specifically, FIG. 10A shows a housing 2 having a proximal end 21 and an opposite distal end 22. The housing may further comprise a protrusion (not illustrated) on its inner wall, which is adapted for receiving a recess of an activation member 3. The recess is used for locking the activation member 3 inside the housing 2, when the activation member 3 is in its most proximal position after an injection of medicament has been made. The housing 2 may further comprise a container holder 24 which is coaxially arranged and fixed attached within the housing 2 for lodging a medicament container 60.

FIG. 10B shows the activation member 3 of the medicament delivery device. The activation member 3 comprises an annular contact member 31 and a counterpart protrusion 35. In this figure, there are two counterpart protrusions 35 used for activating the medicament delivery device. The activation member 3 may comprise a guiding means 34 which is adapted to cooperate with a guiding rod (not shown) at the interior of the housing 2, for the purpose of preventing that the activation member 3 may rotate in relation to the tubular housing 2 and of allowing the activation member 3 to move in the axial direction in relation to the housing 2. Preferably, there are two guiding means 34 and correspondingly two guiding rods (not shown) used. A resilient member 62, which in an exemplary embodiment is a tension spring, is arranged at the proximal end of the activation member 3 for moving the member 3 in a proximal direction.

FIG. 10C shows the interior of the medicament delivery device comprising the sub-assembly according to the present disclosure, and a medicament releasing assembly 6. The medicament releasing assembly 6 comprises the resilient member 62 applying forces to move the activation member 3 in a proximal direction. The contact member 31 is in contact with the proximal end of the housing 20 when the medicament delivery device is in an activated state, and the contact member 31 is at a predetermined distance from the proximal end of the housing when the medicament delivery device is in a non-activated state. The medicament container 60 is arranged within the container holder 24, and has a predetermined volume of medicament, a slidable stopper 64 and a delivery member. The medicament container 60 may be a syringe provided with a needle 63 as the delivery member, but not be limited to this. Other embodiments could include a medicament cartridge having a membrane, or the like where a delivery member can be adapted. The proximal end of the plunger rod 11 is in contact with the slidable stopper 64.

In the final assembly, the sub-assembly 1 is inserted into the housing 2. An inner surface of the housing 2 and the first part 125a of the first engagement element 125 interferes with each other, and thus the first part 125a is bent radially inwards. This causes the third and fourth parts 125c, 125d to move or be bent slightly inwards as well. Consequently, the elastic force applied by the third part 125c on the protrusion 142a is also reduced, and force required for initiating a rotation of the coupling member 14 relative to the main body 12 is reduced. This facilitates easy rotation of the coupling member 14 when the medicament delivery device is intentionally activated.

The rotation of the coupling member 14 to release the plunger rod 11 for injection of medicament is performed by interactions between guide channels 146, 147 longitudinally formed on an outer surface of the coupling member 14 and a counterpart protrusion 35 formed on the activation member 3.

As shown in FIG. 8, the first guide channel 146 starts from the proximal end of the coupling member 14 and ends at a middle portion of the coupling member 14. The second guide channel 147 starts from the proximal end 147a of the coupling member 14 and substantially ends close to the distal end of the coupling member 14. The first and second guide channels 146, 147 are disposed adjacent to each other in a circumferential direction of the coupling member 14. The start of the first guide channel 146 has an opening allowing the counterpart protrusion 35 to enter, and the end of the first guide channel 146 has another opening connected to a middle part of the second guide channel 147. Further, the end of the first guide channel 146 has a slanted guide wall 149, which allows the counterpart protrusion 35 to enter the second guide channel 147. The second guide channel 147 guides the counterpart protrusion 35 to move straightly toward the distal end first and then toward the proximal end of the coupling member 14. The start of the second guide channel 147 at the proximal end of the coupling member 14 is closed. A one-way stopper 148 is located adjacent to the start of the second guide channel 147, such that when the counterpart protrusion 35 becomes positioned in a channel space between the start of the second guide channel 147 and the one-way stopper 148, the counterpart protrusion 35 cannot not move in either the proximal or the distal direction.

The activation member 3 is configured to move only straight in the longitudinal direction within the housing 2, such that the counterpart protrusion 35 on the activation member 3 is so. When the activation member 3 moves straight in a distal direction, the counterpart protrusion 35 slides along the first guide channel 146 first, and is then guided toward the second guide channel 147 by the slanted guide wall 149. Since the activation member 3 is configured to move only straightly, the coupling member 14 get rotated by interaction between the slanted guide wall 149 and the counterpart protrusion 35. At this point when the coupling member 14 is rotated counterclockwise, the plunger rod 11 is released.

When the activation member 3 moves back in a proximal direction by force of the resilient member 62, the counterpart protrusion 35 moves along the second guide channel 147 and then reaches the channel space between the closed end of the second guide channel 147 and the one-way stopper 148. In this state, the activation member 3 cannot move in the distal direction, and covers the needle 63.

FIGS. 11A to 11D show different operation states of the medicament delivery device, which includes the sub-assembly 1 according to the present disclosure. FIG. 11A shows an initial non-activated state of the medicament delivery device having a cap 40. FIG. 11B shows an activated state of the medicament delivery device, where the cap 40 is removed. FIG. 11C shows the penetration and injection state of the medicament delivery device 1, and finally FIG. 11D shows the medicament delivery device 1 in a final locked state.

With references to FIG. 11A, the medicament delivery device comprises the housing 2, having a proximal end and an opposite distal end. The medicament injection device further comprises the activation member 3 which is slidably and coaxially arranged inside the housing 2 and comprises the contact member 31. The cap 40 is manually operated and detached just before the activation of the device.

FIG. 11B show the medicament delivery device when it is ready for use, i.e., when the device is about to perform a medicament delivery against a delivery site. The activation member 3 is then moved in the distal direction, in relation to the housing 2, and during the relative movement, a needle 63 then penetrates the skin. When the activation member 3 is about to reach its most distal position in relation to the housing 2, the medicament delivery is performed. A medicament delivery is automatically performed when the activation member 3, being in an activated position, is moved in the distal direction in relation to the housing 2.

FIG. 11C illustrates a moment when the delivery is made, and then the user removes the medicament delivery device from the delivery site. The activation member 3 moves in the proximal direction in relation to the tubular housing 2, by the force exerted by the resilient member 62 and finally reaches a final state, i.e. a locked state.

FIG. 11D illustrates the medicament delivery device in its final and locked state. The activation member 3 once more is in its most proximal position. In this state the proximal part of the activation member 3 fully protects the medicament delivery member (needle) 63, and the activation member 3 is also locked by the engagement between the cut-out/recesses with the protrusion (not illustrated) of the housing 2, and/or by the engagement between the protrusion 35 and the one-way stopper 148. In the final position, unintentional availability of the medicament delivery member 63 is prevented.

The invention claimed is:

1. A sub-assembly for a medicament delivery device, comprising:

a plunger rod;

a biasing member configured to bias the plunger rod;

a main body arranged to receive the plunger rod and the biasing member and comprising a holding member; and a coupling member arranged to be rotatable relative to the main body, wherein the holding member is configured to have, at least, a holding position in which the holding member is engaged with the plunger rod, and a releasing position in which the holding member is released from the plunger rod, the holding member being switchable from the holding position to the releasing position depending on rotational positions of the coupling member relative to the main body, wherein one of the main body and the coupling member comprises a first engagement element having a protrusion extending substantially radially and forming a hook shape with a longitudinally-extending portion of the first engagement element, and the other one of the main body and the coupling member has a second engagement element which can be engaged with the protrusion, and the main body and the coupling member are configured such that the protrusion of the first engagement element is engaged with the second engagement element to form a snap-fit coupling, such that at least when the holding member is in the holding position, the snap-fit coupling restricts the movement of the coupling member relative to the main body in a proximal direction.

2. The sub-assembly for a medicament delivery device according to claim 1, wherein one end of the first engagement element is fixed to the main body and the other end of the first engagement element is a free end; and the hook shape of the first engagement element comprises, at least, a third part connected to the main body and extending in the proximal direction, and a fourth part extending radially from an end of the third part and forming the free end, the fourth part being said protrusion.

3. The sub-assembly for a medicament delivery device according to claim 2, wherein the first engagement element further comprises a first part fixed to the main body and extending longitudinally in the proximal direction as well as radially outwards, and a second part extending radially inwards from an end of the first part and connected to the third part.

4. The sub-assembly for a medicament delivery device according to claim 1, wherein the coupling member includes a rim surrounding a bore at a distal end portion thereof, the rim comprising a recess or hole formed along a circumferential direction of the rim, and the second engagement element comprises a portion of the rim adjacent to the recess or hole.

5. The sub-assembly for a medicament delivery device according to claim 4, wherein the coupling member has a releasing rotational position and a holding rotational position, relative to the main body, which respectively correspond to the releasing position and the holding position of the holding member, and when the coupling member is in the releasing rotational position, said protrusion of the first engagement element is engaged with the portion of the rim adjacent to the recess or hole.

6. The sub-assembly for a medicament delivery device according to claim 4, wherein the coupling member further includes at least one protrusion which is formed on an inner surface of the rim and disposed between the distal end of the coupling member and the recess or hole, the second engagement element comprises the at least one protrusion, and said protrusion of the first engagement element is engaged with the protrusion of the coupling member, or with the at least one protrusion and the rim of the coupling member together, adjacent to the recess or hole.

7. The sub-assembly for a medicament delivery device according to claim 6, wherein the coupling member has, at least, a releasing rotational position and a holding rotational position relative to the main body, which respectively correspond to the releasing position and the holding position of the holding member, and when the coupling member is in the holding rotational position, said protrusion of the first engagement element is engaged with the at least one protrusion of the coupling member, or with the at least one protrusion and the rim of the coupling member together, adjacent to the recess or hole.

8. The sub-assembly for a medicament delivery device according to claim 1, wherein the coupling member includes a rim surrounding a bore at the distal end portion thereof, and comprising a recess or hole formed along a circumferential direction of the rim, the coupling member further includes at least one protrusion which is formed on an inner surface of the rim and disposed between the distal end of the coupling member and the recess or hole, the second engagement element comprises at least the protrusion of the coupling member, the coupling member has a releasing rotational position and a holding rotational position, relative to the main body, which respectively correspond to the releasing position and the holding position of the holding member, and when the coupling member is in the releasing rotational position, said protrusion of the first engagement element is not engaged with the rim, or engaged with the rim only; and when the coupling member is in the holding rotational position, said protrusion of the first engagement element is engaged at least with the at least one protrusion.

9. The sub-assembly for a medicament delivery device according to claim 1, wherein the coupling member comprises a central through-hole into which the main body can be inserted, and a longitudinal groove which can guide the insertion of the main body into the coupling member, and the coupling member is rotatable relative to the main body when the main body is inserted into the coupling member along the longitudinal groove up to a pre-determined fully-inserted position.

10. The sub-assembly for a medicament delivery device according to claim 9, wherein the coupling member is in the releasing rotational position when the main body is inserted into the coupling member up to the pre-determined fully-inserted position, and the coupling member is in the holding rotational position when the coupling member is rotated in a first rotational direction by a pre-set angle from the pre-determined fully-inserted position.

11. The sub-assembly for a medicament delivery device according to claim 8, wherein the at least one protrusion of the coupling member includes two protrusions which form a recess between the two protrusions, and the first engagement element is disposed to be in or face the recess when the main body is inserted into the coupling member up to a pre-determined fully-inserted position.

12. The sub-assembly for a medicament delivery device according to claim 11, wherein one of the two protrusions is configured not to be engaged with the protrusion of the first engagement element and has a wall-shaped surface which is configured to restrict a movement of the first engagement element in a rotational direction of the coupling member.

13. The sub-assembly for a medicament delivery device according to claim 8, wherein the protrusion of the coupling member arranged to be engaged with said protrusion of the first engagement element has a ramp-shaped surface which interferes with the first engagement element and thereby guides the protrusion of the first engagement element to move radially inwards while the coupling member is being rotated.

14. The sub-assembly for a medicament delivery device according to claim 4, wherein the recess or hole has a radial edge which restricts a movement of the protrusion of the first engagement element in a rotational direction of the coupling member.

15. A medicament delivery device, comprising:

a casing;

an activation member disposed in the casing and linearly movable along the longitudinal direction of the casing;

a medicament container disposed inside the activation member, containing medicament, and comprising a slidable stopper arranged to push the medicament out of the medicament container, and a medicament delivery member connected with a proximal end portion of the medicament container;

a resilient member arranged to apply force to move the activation member in the proximal direction of the medicament delivery device; and the sub-assembly of any one of the preceding claims, which is coupled to the distal end of the casing, arranged to push the slidable stopper when the plunger rod is released.

16. A sub-assembly for a medicament delivery device, comprising:

a plunger rod;

a biasing member configured to bias the plunger rod;

a main body arranged to receive the plunger rod and the biasing member and comprising a holding member; and a coupling member arranged to be rotatable relative to the main body and comprising a rim surrounding a bore at a distal end portion thereof, the rim comprising a recess or hole formed along a circumferential direction of the rim, wherein the holding member is configured to have, at least, a holding position in which the holding member is engaged with the plunger rod, and a releasing position in which the holding member is released from the plunger rod, the holding member being switchable from the holding position to the releasing position depending on rotational positions of the coupling member relative to the main body, wherein the main body comprises a first engagement element having a protrusion extending substantially radially and forming a hook shape with a longitudinally-extending portion of the first engagement element, wherein the protrusion is engaged with a portion of the rim adjacent to the recess or hole, and wherein the engagement of the protrusion with the recess or hole forms a snap-fit coupling, such that when the holding member is in the holding position, the snap-fit coupling prevents movement of the coupling member relative to the main body in a proximal direction.

17. The sub-assembly of claim 16, wherein the coupling member has a releasing rotational position and a holding rotational position relative to the main body, where when in the releasing rotational position the holding member is in the releasing position, and wherein when the coupling member is in the holding rotational position, the protrusion of the first engagement element is engaged with a protrusion on an inner surface of the rim of the coupling member.

18. The sub-assembly of claim 16, wherein the coupling member comprises a central through-hole into which the main body is be inserted and positioned, where the coupling member further comprises a longitudinal groove on an inside surface that defines a guide for the main body during insertion into the coupling member, and wherein the coupling member is rotatable relative to the main body when the main body is inserted into the coupling member along the longitudinal groove up to a predetermined fully inserted position.

19. The sub-assembly of claim 17, wherein the coupling member is in the releasing rotational position when the main body is inserted into a bore at a distal end portion of the coupling member up to a predetermined fully inserted position, and the coupling member is in the holding rotational position when the coupling member is rotated in a first rotational direction by a pre-set angle from the predetermined fully inserted position.

20. The sub-assembly of claim 16, wherein an inner surface of the rim of the coupling member comprises two protrusions, where one of the two protrusions is configured not to be engaged with the protrusion of the first engagement element and has a wall-shaped surface which is configured to restrict a movement of the first engagement element in a rotational direction of the coupling member.

* * * * *